United States Patent
Witt et al.

(10) Patent No.: US 11,497,848 B2
(45) Date of Patent: Nov. 15, 2022

(54) SYSTEMS AND METHODS TO DETECT CATHETER OCCLUSION

(71) Applicant: Becton, Dickinson and Company, Franklin Lakes, NJ (US)

(72) Inventors: Erik K Witt, Wyckoff, NJ (US); S. Ray Isaacson, Layton, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 852 days.

(21) Appl. No.: 15/477,291

(22) Filed: Apr. 3, 2017

(65) Prior Publication Data

US 2018/0280616 A1    Oct. 4, 2018

(51) Int. Cl.
*A61M 5/168*    (2006.01)
*G16H 20/17*    (2018.01)
(Continued)

(52) U.S. Cl.
CPC ........ *A61M 5/16831* (2013.01); *G16H 20/17* (2018.01); *A61B 2017/00119* (2013.01); (Continued)

(58) Field of Classification Search
CPC .......... A61M 5/16831; A61M 5/16859; A61M 2005/16863; A61M 2005/16872; A61M 2205/3693
See application file for complete search history.

(56) References Cited

U.S. PATENT DOCUMENTS 5,445,630 A * 8/1995 Richmond ............ A61M 5/162
                                                    604/905
5,769,819 A * 6/1998 Schwab .............. A61M 25/008
                                                    604/103
(Continued)

FOREIGN PATENT DOCUMENTS

EP    2777743    9/2014
JP    H0458961   2/1992
(Continued)

OTHER PUBLICATIONS

Arai, et al., "Detection of peripherally inserted central catheter occlusion by in-line pressure monitoring", Paediatric Anaesthesia, vol. 12, No. 7, Sep. 2002, pp. 621-624.
(Continued)

*Primary Examiner* — Laura A Bouchelle
*Assistant Examiner* — John A Doubrava
(74) *Attorney, Agent, or Firm* — Kirton McConkie; Whitney Blair; Kevin Stinger

(57) ABSTRACT

A system to detect occlusion of an intravenous catheter may include a housing, which may include a distal end configured to couple to a proximal end of a catheter adapter and an inner lumen forming a fluid pathway. The system may also include a wave transmitter, a transducer disposed within the fluid pathway, a processor coupled to the transducer, and an indicator unit coupled to the processor. The wave transmitter may transmit energy waves along a length of an intravenous catheter of the catheter adapter. The processor may receive an electrical signal corresponding to the portion of the energy waves that are reflected back from the intravenous catheter and may determine a difference between the electrical signal and a baseline signal. In response to the difference between the electrical signal and the baseline signal meeting a threshold value, the indicator unit may alert a user.

4 Claims, 7 Drawing Sheets

(51) Int. Cl.
*A61M 25/00* (2006.01)
*A61B 17/00* (2006.01)
*A61B 90/00* (2016.01)

(52) U.S. Cl.
CPC ............ *A61B 2090/081* (2016.02); *A61M 2005/16863* (2013.01); *A61M 2025/0019* (2013.01); *A61M 2205/3331* (2013.01); *A61M 2205/3592* (2013.01); *A61M 2205/50* (2013.01); *A61M 2205/58* (2013.01)

(56) References Cited

U.S. PATENT DOCUMENTS

| | | | |
|---|---|---|---|
| 8,147,479 B1 | 4/2012 | Wach et al. | |
| 8,700,133 B2 | 4/2014 | Hann | |
| 2009/0093786 A1* | 4/2009 | Renaux | G01P 13/0086 604/67 |
| 2017/0340801 A1* | 11/2017 | Roger | A61N 1/00 |
| 2017/0356838 A1* | 12/2017 | Knollenberg | H05B 47/115 |
| 2018/0236165 A1* | 8/2018 | Dearmond | A61M 5/16854 |

FOREIGN PATENT DOCUMENTS

| | | |
|---|---|---|
| JP | 2014176689 | 9/2014 |
| JP | 2015/157191 | 10/2015 |
| JP | 2016214793 | 12/2016 |
| WO | 2008100671 | 8/2008 |
| WO | 2015/157191 | 10/2015 |
| WO | 2017/031394 | 2/2017 |

OTHER PUBLICATIONS

Wolf, et al., "Monitoring Central Venous Catheter Resistance to Predict Imminent Occlusion: A Prospective Pilot Study," PLOS ONE, vol. 10, No. 8, Aug. 31, 2015.

* cited by examiner

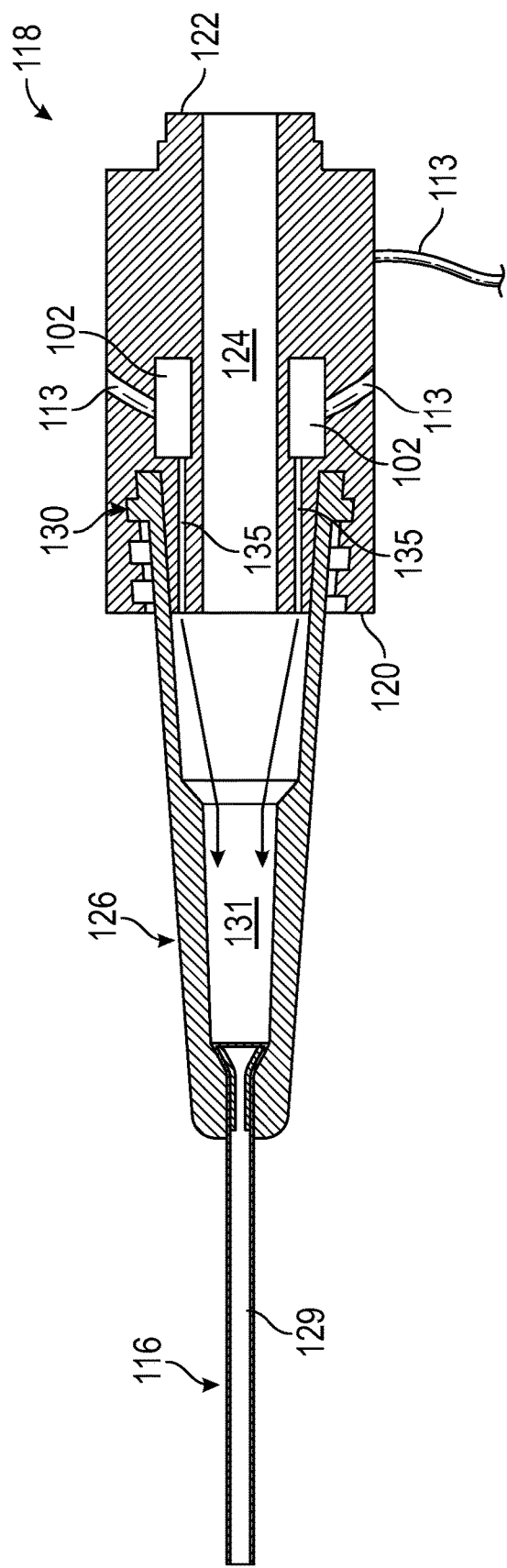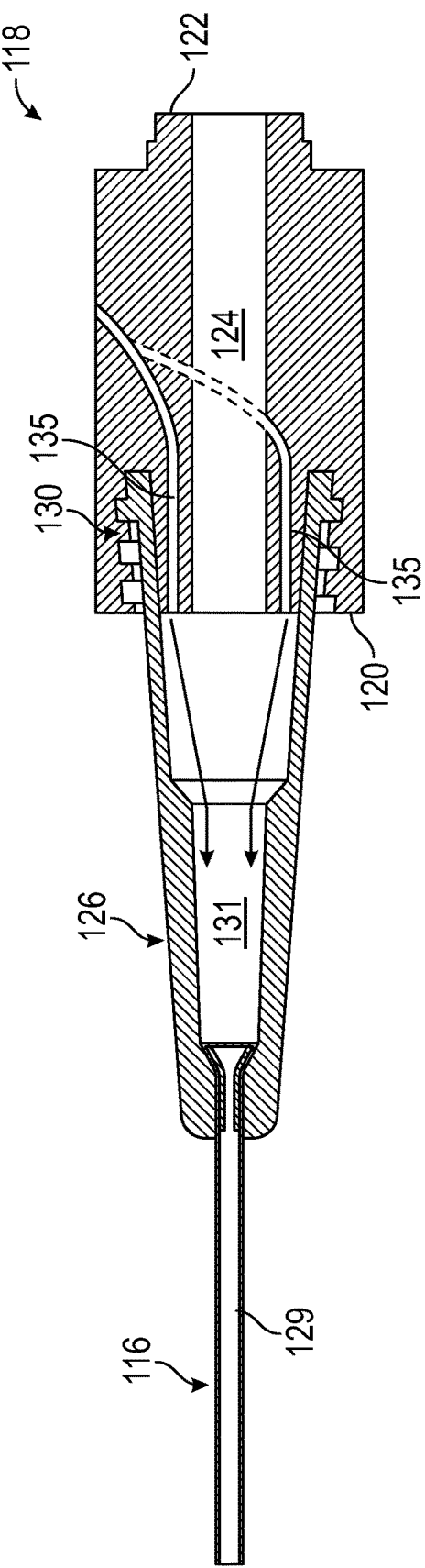
FIG. 2D
FIG. 2E

SYSTEMS AND METHODS TO DETECT CATHETER OCCLUSION

BACKGROUND OF THE INVENTION

In some instances, an intravenous (IV) catheter, including a peripheral IV catheter, may become unusable or compromised prior to completion of infusion or blood withdrawal using the catheter. One reason the catheter may become unusable may be due to occlusion of the catheter over time. In response to the catheter becoming occluded, the catheter may need to be removed and replaced with a new catheter. Catheter occlusions may be thrombotic, resulting from formation of a thrombus within or surrounding a distal tip of the catheter. Catheter occlusions may also be non-thrombotic, resulting from precipitates, mechanical obstructions, and other factors. Further, catheter occlusions can lead to catheter infection, pulmonary embolism, post-thrombotic syndrome, and other negative health outcomes.

Accordingly, there is a need in the art for devices, systems, and methods that provide an early indication of catheter occlusion and allow a clinician to establish a new intravenous line before an old intravenous line is ineffective or dangerous to a patient. Such devices, systems, and methods are disclosed in the present disclosure.

BRIEF SUMMARY OF THE INVENTION

The present disclosure relates generally to detection of IV catheter occlusion. In particular, the present disclosure relates to devices, systems, and associated methods to detect IV catheter occlusion. In some embodiments, a system to detect occlusion of an intravenous catheter may include a housing, which may include a distal end, a proximal end, and an inner lumen forming a fluid pathway. In some embodiments, the inner lumen may extend between the distal end and the proximal end of the housing.

In some embodiments, the system may include a catheter adapter. In some embodiments, the catheter may extend distally from a distal end of the catheter adapter. In some embodiments, the fluid pathway may extend through an inner lumen of the catheter and the catheter adapter. In some embodiments, the distal end of the housing may be configured to couple to a proximal end of the catheter adapter. In some embodiments, the housing may be integrally formed with the catheter adapter and/or may include or correspond to a portion of the catheter adapter.

In some embodiments, the housing may include one or more wave transmitters, which may transmit electromagnetic or energy waves along a length of the catheter of the catheter adapter. In some embodiments, the housing may include one or more transducers, which may detect a portion of the energy waves that are reflected back from the catheter. In some embodiments, the one or more transducers may be disposed in any location within the housing that allows the one or more transducers to detect the portion of the energy waves that are reflected back from the catheter. In some embodiments, one or more transmitters may be disposed in any location within the housing that allows them to transmit the energy waves along the length of the catheter. In some embodiments, the one or more transducers may be embedded or encapsulated in a wall of the inner lumen of the housing. In some embodiments, the one or more transducers may be disposed in the fluid pathway, disposed partially within the fluid pathway, or separated from the fluid pathway by a buffer element, such as, for example, a membrane, coating, adhesive, or another suitable element.

In some embodiments, the system may include a processor, which may be coupled to the one or more transducers. In some embodiments, the processor may receive an electrical signal corresponding to the portion of the energy waves that are reflected back from the catheter. In some embodiments, the processor may compare the electrical signal to a baseline electrical signal to determine a difference between the electrical signal and the baseline electrical signal.

In some embodiments, the system may include an indicator unit, which may be coupled to the processor. In some embodiments, in response to the difference between the electrical signal and the baseline electrical signal meeting a threshold value, the indicator unit may alert a user. For example, the indicator unit may sound an alarm and/or generate a warning message, which may be displayed and/or audibly conveyed to the user.

In some embodiments, the one or more wave transmitters may include an ultrasound wave transmitter that transmits ultrasonic waves. In some embodiments, the one or more wave transmitters may include an sonic wave transmitter that transmits sonic waves. In some embodiments, the one or more wave transmitters may include an electromagnetic wave transmitter that transmits electromagnetic waves, including, radio waves, microwaves, infrared, visible light, ultraviolet, X-rays, or gamma rays. In some embodiments, the electromagnetic wave transmitter may include an invisible light source, such as, for example, an infrared or ultraviolet laser, emitting an invisible light beam. In some embodiments, the electromagnetic wave transmitter may include a visible light source, such as, for example, a He—Ne laser, emitting a visible light beam.

In some embodiments, the one or more transducers may each include an ultrasound transducer that may detect ultrasound waves reflected from the catheter. In some embodiments, the one or more transducers may each include a sonic transducer that may detect sonic waves reflected from the catheter. In some embodiments, the one or more transducers may include an electromagnetic wave transducer. For example, the one or more transducers may each include a light transducer, such as, for example, a photodiode, that may detect light waves reflected from the catheter. In some embodiments, the one or more transducers may convert the portion of the energy waves that are reflected back from the catheter to the electrical signal.

In some embodiments, the one or more transducers may each include a piezoelectric element, such as, for example, a piezoelectric crystal. In some embodiments, a particular piezoelectric element may transmit ultrasonic waves along the length of the catheter. In some embodiments, a same or different piezoelectric element may receive the portion of the ultrasonic waves that are reflected back from the catheter and convert the portion to a corresponding electrical signal.

In some embodiments, the baseline electrical signal may be determined by transmitting, via the wave transmitter, which may include the one or more ultrasonic transducers, other ultrasonic waves along the length of the catheter when the catheter is open or unoccluded and converting a portion of the other ultrasonic waves that are reflected back from the catheter to the baseline electrical signal. In some embodiments, the baseline electrical signal may be determined prior to transmitting the energy waves along the length of the intravenous catheter and/or converting the portion of the energy waves that are reflected back from the intravenous catheter to the corresponding electrical signal. For example, the baseline electrical signal may be determined immediately after or shortly after insertion of the catheter into a vein of the patient.

In some embodiments, an outer surface of a distal tip of the intravenous catheter may be facetted, including one or more facets, which may improve reflection of the energy waves. In some embodiments, a wall forming the inner lumen of the catheter may be facetted, including one or more facets, which may improve reflection of the energy waves.

BRIEF DESCRIPTION OF THE SEVERAL VIEWS OF THE FIGURES

In order that the manner in which the above-recited and other features and advantages of the invention will be readily understood, a more particular description of the systems and methods to detect catheter occlusion briefly described above will be rendered by reference to specific embodiments thereof, which are illustrated in the appended Figures. Understanding that these Figures depict only typical embodiments and are not, therefore, to be considered to be limiting of its scope, the invention will be described and explained with additional specificity and detail through the use of the accompanying Figures in which:

FIG. 2D illustrates another cross-sectional view of the portion of the system, according to some embodiments;

FIG. 2E illustrates another cross-sectional view of the portion of the system, according to some embodiments;

DETAILED DESCRIPTION OF THE INVENTION

The presently preferred embodiments of the described invention will be best understood by reference to the Figures, wherein like parts are designated by like numerals throughout. It will be readily understood that the components of the present invention, as generally described and illustrated in the Figures herein, could be arranged and designed in a wide variety of different configurations. Thus, the following more detailed description of the embodiments, represented in FIGS. 1 through 4, is not intended to limit the scope of the invention, as claimed, but is merely representative of some embodiments of the invention.

Figure 1A:
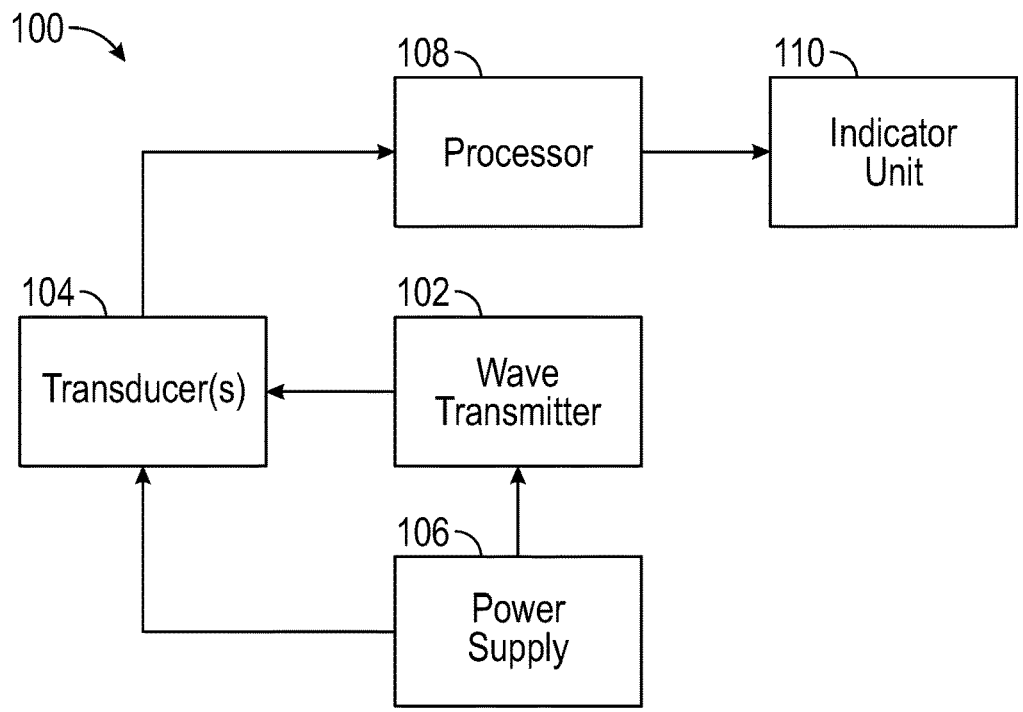
FIG. 1A illustrates a block diagram of an example system to detect catheter occlusion, according to some embodiments.

Generally, the present disclosure relates generally to detection of IV catheter occlusion or conditions within an IV catheter that may lead to occlusion. In particular, the present disclosure relates to devices, systems, and associated methods to detect IV catheter occlusion or conditions within the IV catheter that may lead to occlusion. Referring now to FIG. 1A, in some embodiments, a self-diagnosing catheter assembly or system 100 may include a wave transmitter 102, which may transmit electromagnetic or energy waves along a length of an intravenous catheter of a catheter adapter. In some embodiments, the wave transmitter 102 may generate and/or transmit the energy waves along the length of the catheter when the catheter is tested for occlusion. In some embodiments, the catheter may be tested for occlusion after the catheter has been inserted into a vein of a patient for any period of time.

In some embodiments, the system 100 may include one or more transducers 104. In some embodiments, the wave transmitter 102 and/or the transducers 104 may be in a fluid pathway of a housing, partially within the fluid pathway, or separated from the fluid pathway by a buffer element, such as, for example, a membrane, coating, adhesive, or another suitable element. In some embodiments, the housing may be coupled with the catheter adapter. In some embodiments, the housing may be integrally formed with the catheter adapter and/or may include or correspond to a portion of the catheter adapter. In some embodiments, the one or more transducers 104 may detect a portion of the energy waves that are reflected back from the catheter. In some embodiments, the wave transmitter 102 and/or the one or more transducers 104 may be coupled with a power supply 106. In some embodiments, the system 100 may not include the housing. In these and other embodiments, the one or more transducers 104 and/or the wave transmitter 102 may be disposed within the catheter adapter 126.

In some embodiments, the system 100 may include a processor 108, which may be coupled to the one or more transducers 104. In some embodiments, the processor 108 may receive an electrical signal corresponding to the portion of the energy waves that are reflected back from the catheter. In some embodiments, the processor 108 may compare the electrical signal to a baseline electrical signal to determine a difference between the electrical signal and the baseline electrical signal.

In some embodiments, the baseline electrical signal may be determined by transmitting, via the wave transmitter 102, which may include the ultrasonic transducer, other ultrasonic waves along the length of the catheter when the catheter is unoccluded and converting a portion of the other ultrasonic waves that are reflected back from the catheter to the baseline electrical signal. In some embodiments, the baseline electrical signal may be determined prior to transmitting the energy waves along the length of the catheter and/or converting the portion of the energy waves that are reflected back from the catheter to the corresponding electrical signal. For example, the baseline electrical signal may be determined immediately after or shortly after insertion of the catheter into the vein of the patient. In some embodiments, the baseline electrical signal may be determined using another catheter similar or identical to the catheter. In some embodiments, the other ultrasonic waves may be equivalent to the ultrasonic waves. For example, the other ultrasonic waves and the ultrasonic waves may have the same frequency, amplitude, etc.

In some embodiments, the difference between the electrical signal and the baseline electrical signal may correspond to a difference in amplitude and/or frequency between the portion of the ultrasonic waves that are reflected back from the catheter when the catheter is tested for occlusion and the portion of the other ultrasonic waves that are reflected back from the intravenous catheter when the catheter is unoccluded. In some embodiments, the difference between the electrical signal and the baseline electrical signal may be due to a state change within the catheter. For example, a larger difference between the electrical signal and the baseline signal may occur in response to presence of one or more blood clots within the catheter. In some embodiments, the larger the difference, the more likely the catheter is occluded or likely to become occluded.

In some embodiments, the system 100 may include an indicator unit 110, which may be coupled to the processor 108. In some embodiments, in response to the difference between the electrical signal and the baseline electrical signal meeting a threshold value, the indicator unit 110 may alert a user. For example, the indicator unit 110 may sound an alarm and/or generate a warning message, which may be displayed and/or audibly conveyed to the user. In some embodiments, the alarm and/or the message may indicate to the user that the catheter should be changed to a new catheter. In some embodiments, the indicator unit 110 may include a display, which may be disposed on the housing or another element of the system, and which may be configured to present the warning message to the user. In some embodiments, the threshold value may indicate a likelihood of occlusion of the catheter or a state of the blood within the catheter that is likely to lead to occlusion.

In some embodiments, the wave transmitter 102 may include an ultrasound wave transmitter that transmits ultrasonic waves. In some embodiments, the wave transmitter 102 may include a sonic wave transmitter that transmits sonic waves. In some embodiments, the wave transmitter 102 may include an electromagnetic wave transmitter that transmits electromagnetic waves including, radio waves, microwaves, infrared, visible light, ultraviolet, X-rays, or gamma rays. In some embodiments, the electromagnetic wave transmitter may include an invisible light source, such as, for example, an infrared or ultraviolet laser, emitting an invisible light beam. In some embodiments, the electromagnetic wave transmitter may include a visible light source, such as, for example, a He—Ne laser or another type of laser, emitting a visible light beam.

In some embodiments, the one or more transducers 104 may each include an ultrasound transducer that may detect ultrasound waves reflected from the catheter. In some embodiments, the one or more transducers may include an electromagnetic wave transducer. For example, the one or more transducers 104 may each include a light transducer, such as, for example, a photodiode, that may detect light waves reflected from the catheter. In some embodiments, the one or more transducers 104 may convert the portion of the energy waves that are reflected back from the catheter to the electrical signal.

Figure 1B:
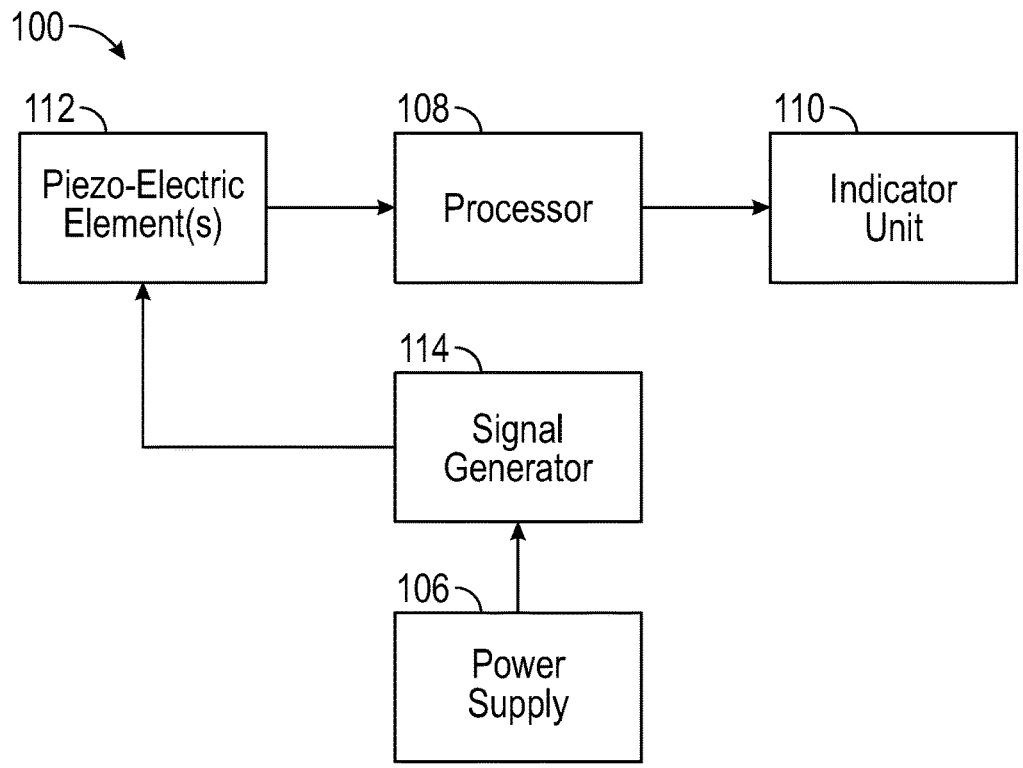
FIG. 1B illustrates a block diagram of the system, according to some embodiments.

Referring now to FIG. 1B, in some embodiments, the one or more transducers 104 of FIG. 1A may each include a piezoelectric element 112, such as, for example, a piezoelectric crystal. In some embodiments, one or more piezoelectric elements 112 may act as the wave transmitter 102. In some embodiments, a particular piezoelectric element 112 may transmit ultrasonic waves along the length of the catheter. In some embodiments, a same or different piezoelectric element 112 may receive the portion of the ultrasonic waves that are reflected back from the catheter and convert the portion to a corresponding electrical signal.

In some embodiments, the system 100 may include a signal generator 114, which may be coupled to the power supply 106 and the one or more piezoelectric elements. In some embodiments, the signal generator 114 may excite the one or more piezoelectric elements, which may result in propagation of the ultrasonic waves throughout the inner lumen of the catheter and/or one or more other portions of the fluid pathway. The propagation of the ultrasonic waves may provide vibration of fluid within the fluid pathway, which may be easily altered by presence of one or more clots within the catheter.

Figure 2A:
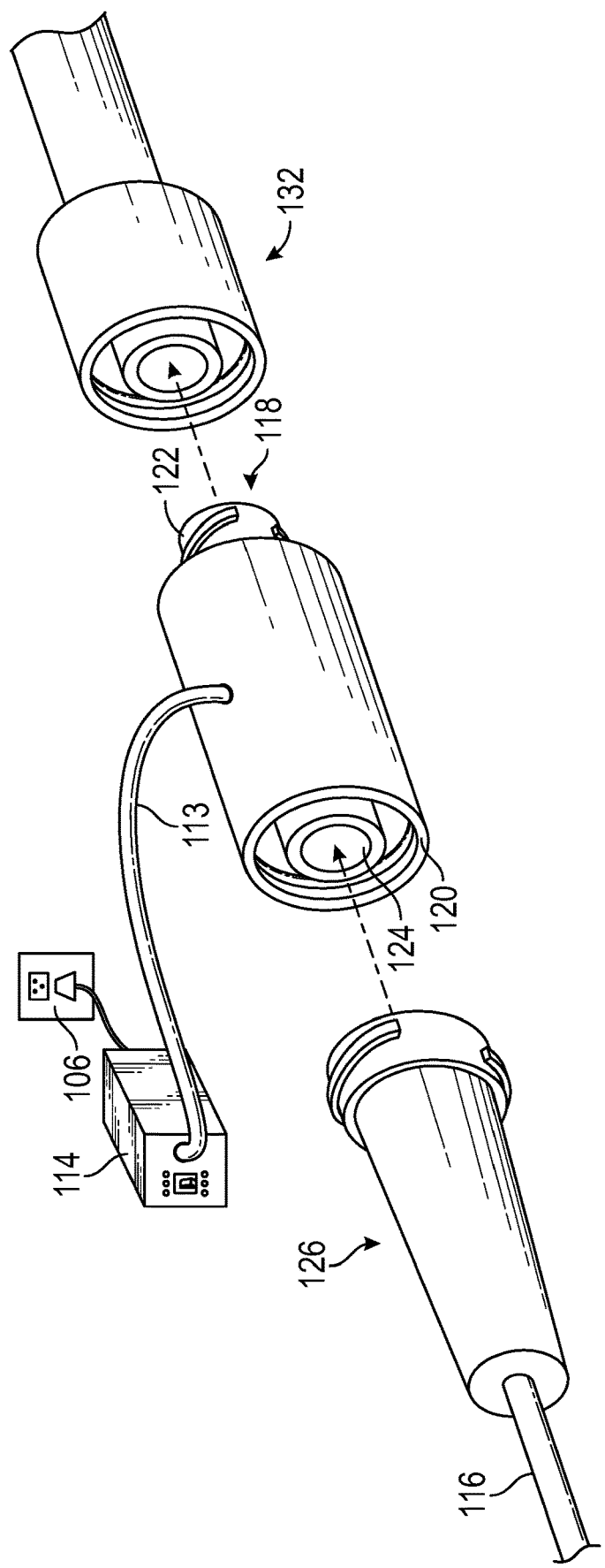
FIG. 2A illustrates an exploded view of the system, according to some embodiments.
Figure 2B:
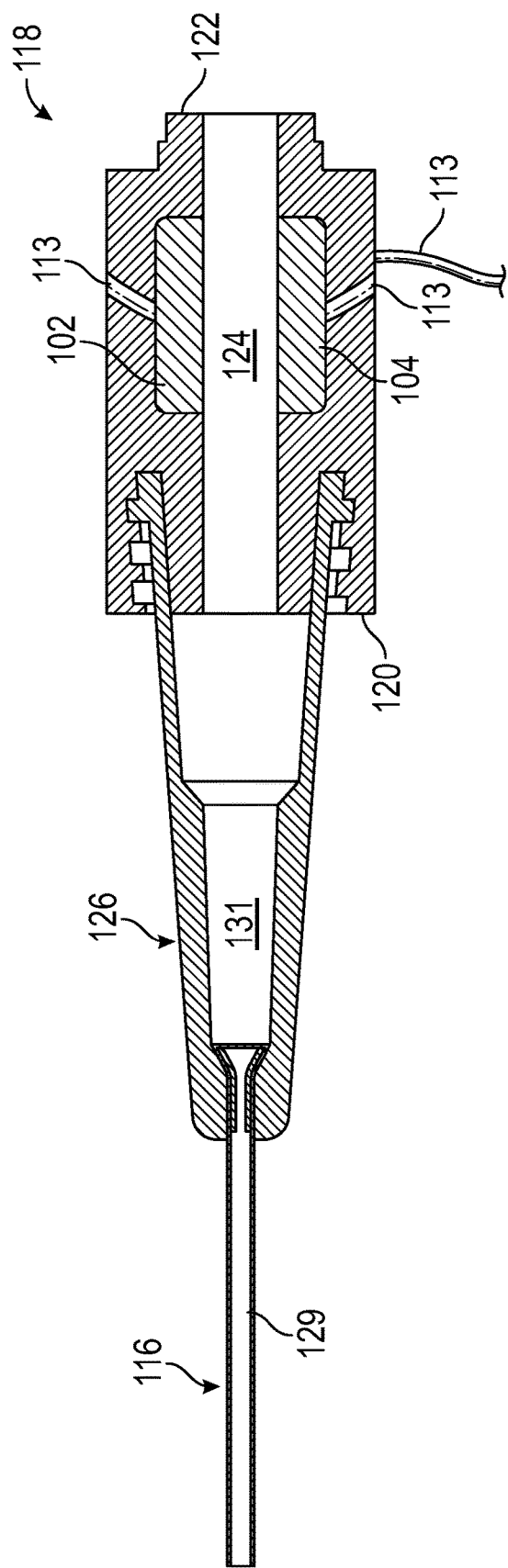
FIG. 2B illustrates a cross-sectional view of a portion of the system, according to some embodiments.

Referring now to FIGS. 2A-2B, in some embodiments, the system 100 to detect occlusion of the catheter 116 may include a housing 118, which may include a distal end 120, a proximal end 122, and an inner lumen 124 forming a fluid pathway. In some embodiments, the inner lumen 124 may extend between the distal end 120 and the proximal end 122 of the housing 118.

In some embodiments, the system 100 may include a catheter adapter 126. In some embodiments, the catheter 116 may extend distally from a distal end 128 of the catheter adapter 126. In some embodiments, the fluid pathway may extend through an inner lumen 129 of the catheter 116 and an inner lumen 131 of the catheter adapter 126, which may be continuous. In some embodiments, the distal end 120 of the housing 118 may be configured to couple to a proximal end 130 of the catheter adapter 126. In some embodiments, the proximal end 130 of the catheter adapter 126 and the distal end 120 of the housing 118 may be threadedly coupled together. In some embodiments, the proximal end 122 of the housing 118 may be configured to receive an IV line via a Luer device 132, which may be threadedly coupled to the proximal end 122.

Figure 2C:
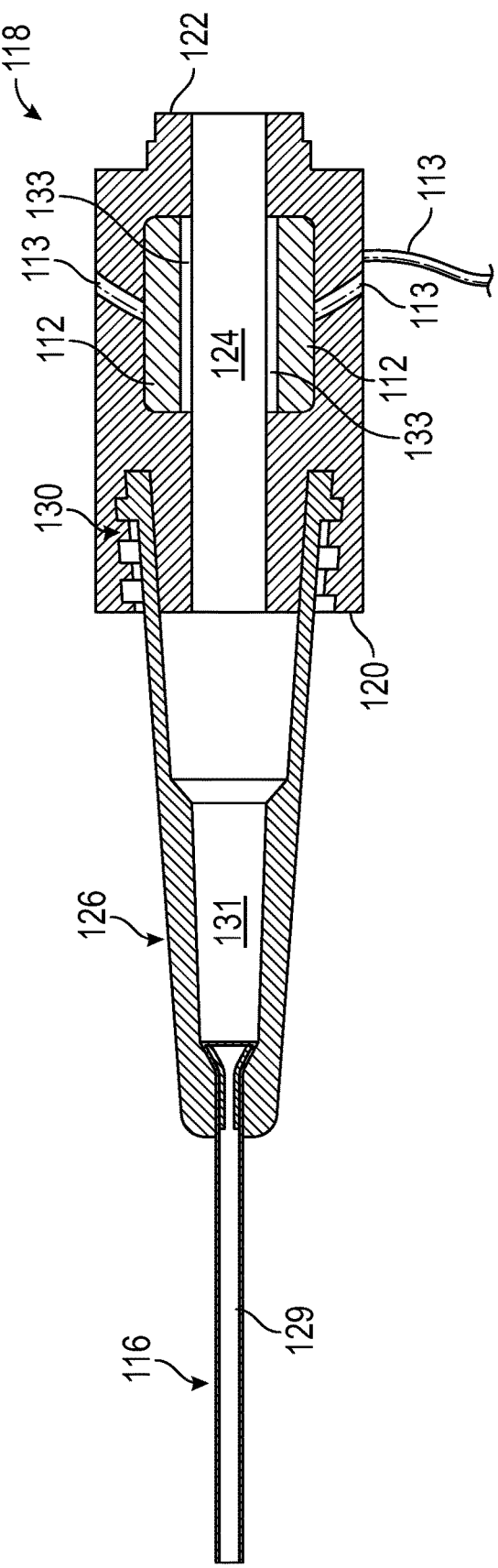
FIG. 2C illustrates another cross-sectional view of the portion of the system, according to some embodiments.

In some embodiments, the system 100 may include one or more piezoelectric elements 112 or one or more other transducers, which may be disposed in the fluid pathway of the housing 118 or capable of sensing energy waves in the fluid pathway. In some embodiments, the one or more piezoelectric elements 112 may include piezoelectric crystals. In some embodiments, the one or more piezoelectric elements 112 or the one or more other transducers may detect a portion of the energy waves that are reflected back from the catheter 116. In some embodiments, the one or more piezoelectric elements 112 or the one or more other transducers may be embedded or encapsulated in a wall of the inner lumen 124 of the housing 118. In some embodiments, the piezoelectric elements 112 may be separated from the fluid pathway by a barrier or buffer element 133, such as, for example, a membrane, coating, adhesive, or other suitable element, as illustrated in FIG. 2C.

In some embodiments, the one or more piezoelectric elements 112 may transmit energy waves along an entire length of the catheter 116 of the catheter adapter 126 and/or throughout an entire lumen 129 of the catheter 116. Thus, in some embodiments, the one or more piezoelectric elements 112 may act as the wave transmitter 102 of FIG. 1A and/or the one or more transducers 104 of FIG. 1A. In some embodiments, the signal generator 114 may be electrically coupled to the one or more piezoelectric elements 112 via one or more connectors or cables 113, which may extend through an opening in the housing 118.

Referring now to FIG. 2D, in some embodiments, the wave transmitter 102 may be disposed in the wall of the housing 118, and the energy waves may be transmitted from the wave transmitter 102 along the length of one or more of the following via one or more wave guides 135: the housing 118, the catheter adapter 126, and the catheter 116. In these and other embodiments, the energy waves may include infrared, visible light, ultraviolet light, or other electromagnetic waves. As illustrated in FIG. 2D, in some embodiments, the wave guides 135 may extend from the wave transmitter 102 through the wall of the housing 118 to a distal end of the housing 118. In some embodiments, the energy waves travelling along the wave guides 135 may emerge at the distal end of the housing and continue through the catheter adapter 126 and/or the catheter 116. In some embodiments, the wave guides 135 may include light guides or optical fibers.

Referring now to FIG. 2E, in some embodiments, the wave transmitter 102 may be external to the housing 118 and/or the catheter adapter 126. In some embodiments, the energy waves may be transmitted from the external wave transmitter 102 through the wall of the housing 118 via the one or more wave guides 135. In some embodiments, the wave guides 135 may extend through the wall of the housing 118 to the distal end of the housing. In some embodiments, the energy waves travelling along the wave guides 135 may emerge at the distal end of the housing and continue through the catheter adapter 126 and/or the catheter 116. Referring to both FIGS. 2D and 2E, in some embodiments, the one or more transducers 104 may be disposed as illustrated in FIG. 2B or 2C or in any location within the housing 118 that allows the one or more transducers 104 to detect the portion of the energy waves that are reflected back from the catheter 116.

Figure 3A:
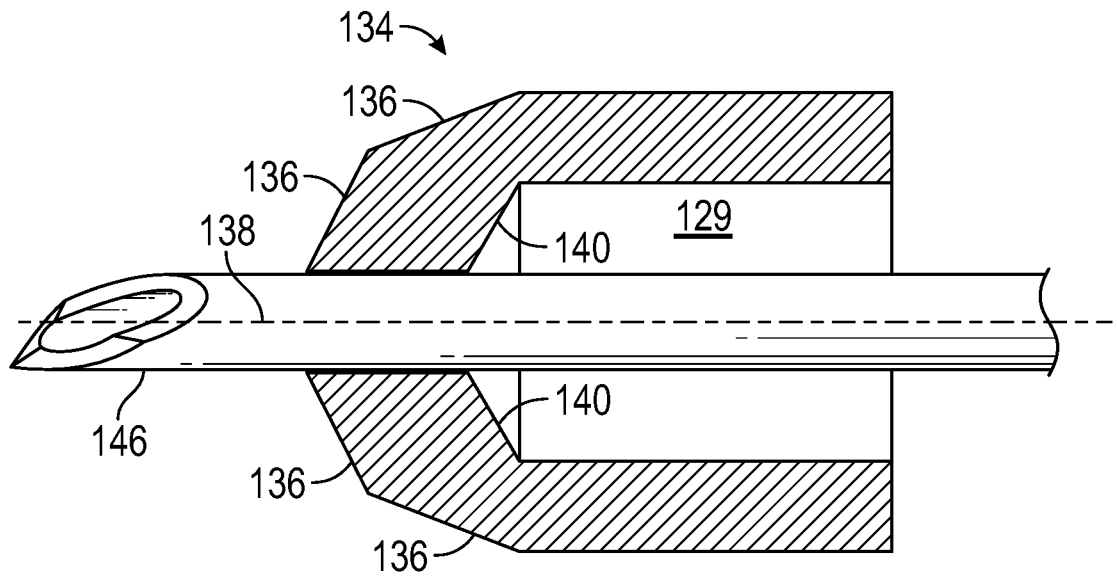
FIG. 3A illustrates a cross-sectional view of an example distal tip of an example catheter of the system, according to some embodiments.

Referring now to FIG. 3A, in some embodiments, an outer surface of a distal tip 134 of the catheter 116 may include one or more outer facets 136 or flat surfaces, which may be angled with respect to a longitudinal axis 138 of the catheter 116. In some embodiments, the facets 136 may improve reflection of the energy waves. Additionally or alternatively, in some embodiments, a wall forming the inner lumen 129 of the catheter 116 may include one or more inner facets 140, which may improve the reflection of the energy waves. In some embodiments, the inner facets 140 may be proximal to and proximate a portion of the tip 134 configured to contact an introducer needle 146 when the introducer needle 146 is inserted into a vein of the patient and prior to withdrawal of the introducer needle. In some embodiments, the outer surface and/or the inner surface of the distal tip 124 may be symmetric about the longitudinal axis 138.

Figure 3B:
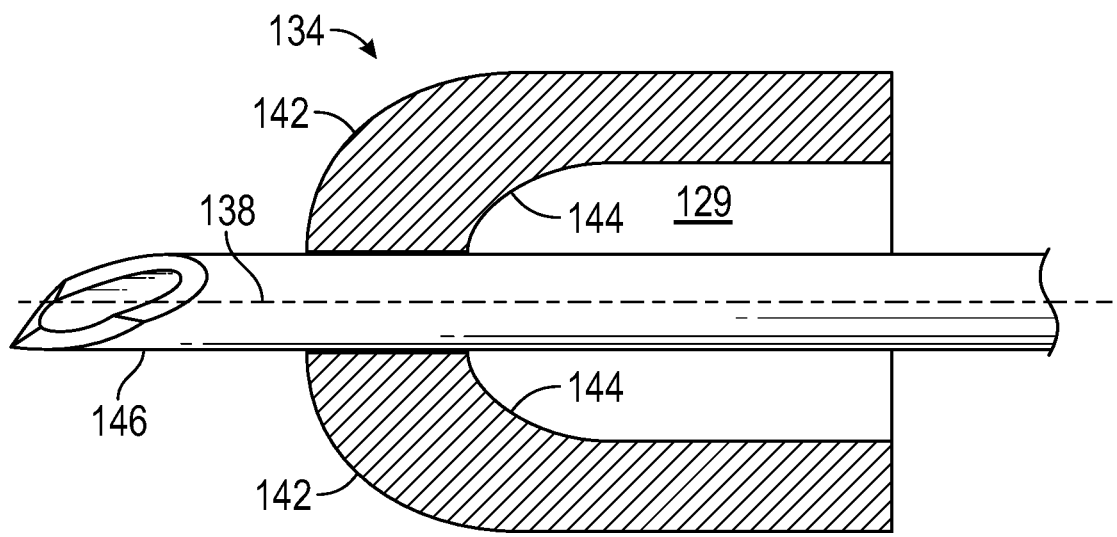
FIG. 3B illustrates a cross-sectional view of another example distal tip of an example catheter of the system, according to some embodiments.

Referring now to FIG. 3B, in some embodiments, an outer surface of the distal tip 134 of the catheter 116 may include one or more outer curved portions 142, which may improve reflection of the energy waves. Additionally or alternatively, in some embodiments, the wall forming the inner lumen 129 of the catheter 134 may include one or more inner curved portions 144, which may improve the reflection of the energy waves. In some embodiments, the inner curved portions 114 may extend from a portion of the tip 134 configured to contact an introducer needle 146 proximally to a proximal end of the catheter 116. The contact between the portion of the tip 134 and the introducer needle 146 may occur when the introducer needle 146 is inserted into a vein of the patient and prior to withdrawal of the introducer needle.

Figure 3C:
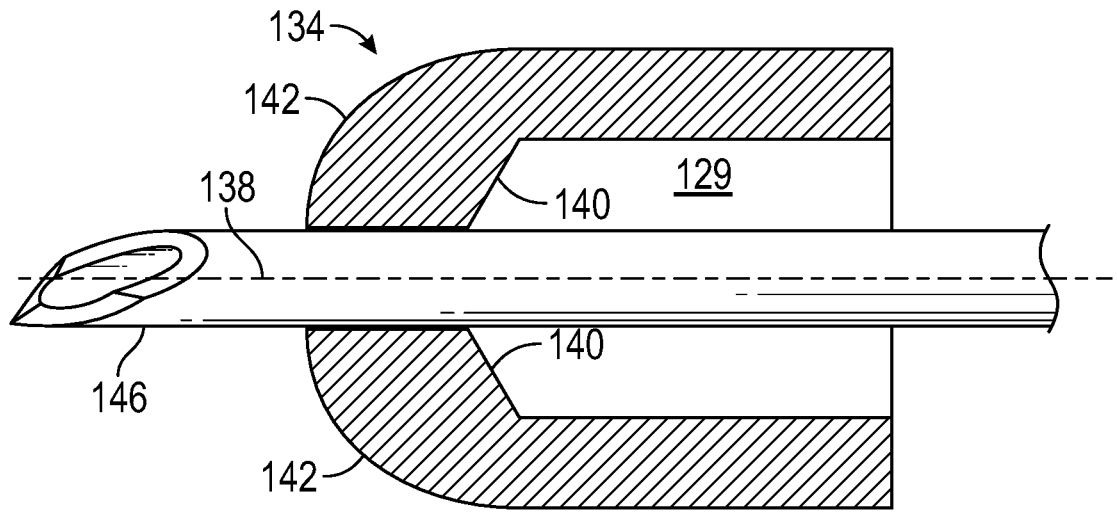
FIG. 3C illustrates a cross-sectional view of another example distal tip of an example catheter of the system, according to some embodiments.
Figure 3D:
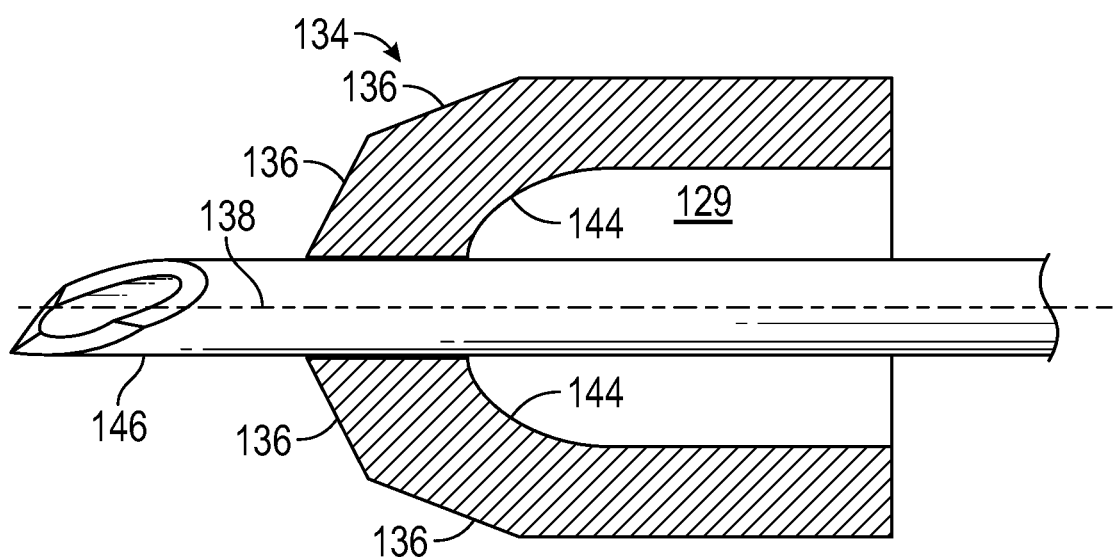
FIG. 3D illustrates a cross-sectional view of another example distal tip of an example catheter of the system, according to some embodiments.

Referring now to FIG. 3C, in some embodiments, the distal tip 134 may include the outer curved portions 142 and the inner facets 140, which may improve the reflection of the energy waves. Referring now to FIG. 3D, in some embodiments, the distal tip 134 may include the outer facets 136 and the inner curves 144, which may improve the reflection of the energy waves.

Figure 4:
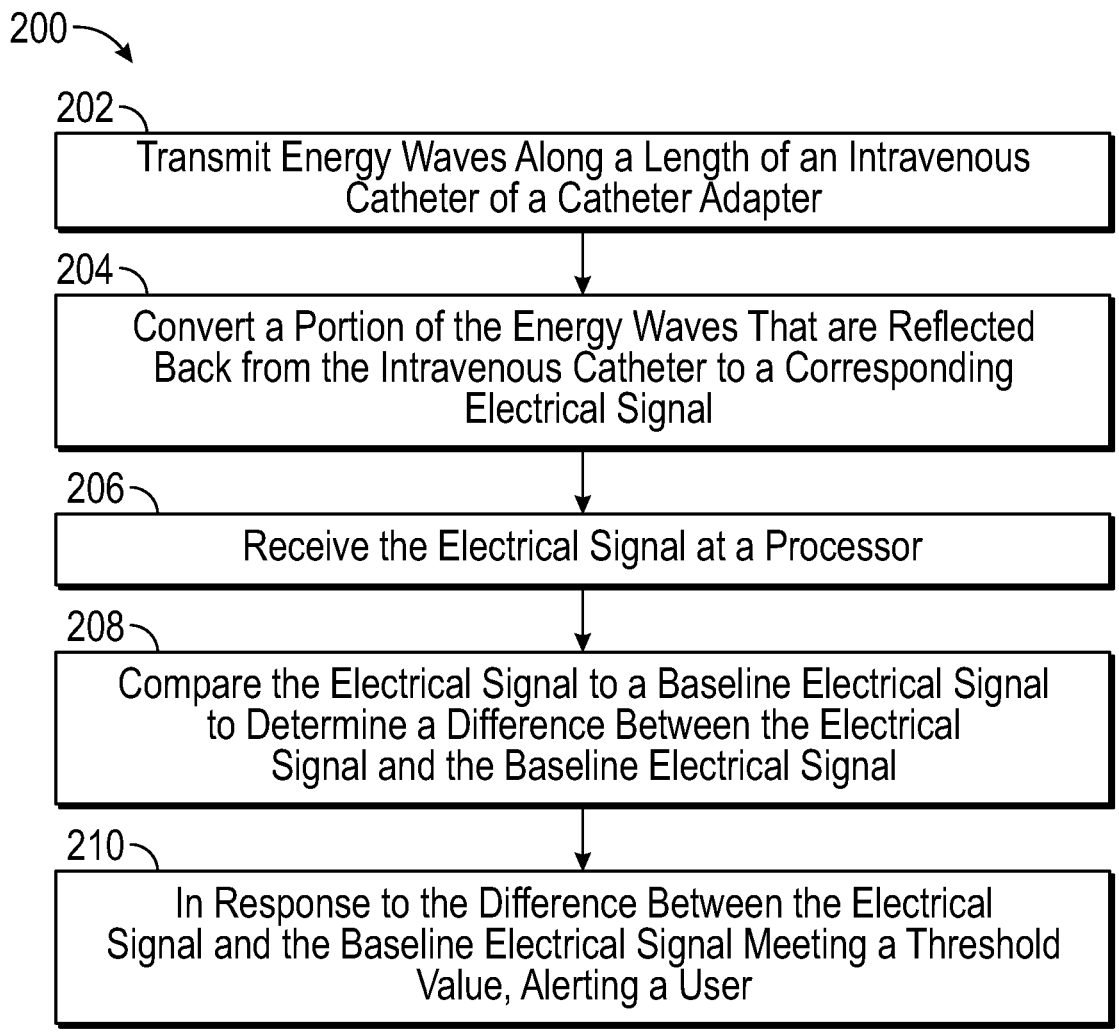
FIG. 4 illustrates a block diagram of an example method to detect catheter occlusion using the system, according to some embodiments.

Referring now to FIG. 4, an example method 200 of detecting IV catheter occlusion or conditions within an IV catheter that may lead to occlusion may begin at block 202 in which energy waves may be transmitted along a length of an IV catheter coupled with a catheter adapter. In some embodiments, the catheter and catheter adapter may include or correspond to the catheter 116 and the catheter adapter 126 of FIGS. 2A-2B. Block 202 may be followed by block 204.

At block 204, a portion of the energy waves that are reflected back from the catheter may be converted to a corresponding electrical signal. Block 204 may be followed by block 206.

At block 206, the electrical signal may be received at a processor. Block 206 may be followed by block 208. The processor may include or correspond to the processor 108 of FIG. 1. At block 208, the electrical signal may be compared to a baseline electrical signal to determine a difference between the electrical signal and the baseline electrical signal. Block 208 may be followed by block 210.

At block 210, in response to the difference between the electrical signal and the baseline electrical signal meeting a threshold value, a user may be alerted.

Although illustrated as discrete blocks, various blocks may be divided into additional blocks, combined into fewer blocks, or eliminated, depending on the desired implementation. In some embodiments, the method 200 may include additional blocks. For example, in some embodiments, the method 200 may include providing one or more of the following: a housing, a transducer, and the catheter adapter. In some embodiments, the housing may include or correspond to the housing 118 of FIGS. 2A-2B, and the transducer may include or correspond to the transducer 104 of FIG. 1A. As another example, in some embodiments, the method 200 may include determining the baseline electrical signal, wherein determining the baseline electrical signal comprises transmitting other energy waves along the length of the intravenous catheter when the intravenous catheter is unoccluded and converting a portion of the other energy waves that are reflected back from the intravenous catheter to the baseline electrical signal.

The present invention may be embodied in other specific forms without departing from its structures, methods, or other essential characteristics as broadly described herein and claimed hereinafter. In some embodiments, the housing 118 of FIGS. 1-2 may not be directly coupled to the catheter adapter 126 and/or the luer device 132. For example, the system 100 of FIGS. 1-2 may include a needle safety mechanism, which may be disposed in between the catheter adapter 126 and the housing 118 or at another location. As another example, the catheter adapter 126 may include various configurations. In some embodiments, the catheter adapter 126 may include a side port, a septum, a septum actuator, or one or more other elements. The described embodiments and examples are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

What is claimed is:
1. A system for detecting occlusion of a catheter comprising:
 a catheter adapter having a proximal end and a distal end;
 a catheter that extends distally from the distal end of the catheter adapter;

a housing having a proximal end, a distal end, and a wall comprising an inner surface forming an inner lumen of the housing that extends between the proximal end of the housing and the distal end of the housing to thereby provide a fluid pathway into the catheter when the housing is coupled to the catheter adapter;

one or more transmitters positioned in the wall, the one or more transmitters emitting electromagnetic signals into the inner lumen of the housing in a distal direction;

one or more transducers that receive the electromagnetic signals after the electromagnetic signals have been reflected by the catheter; and a processor that analyses the reflected electromagnetic signals to detect when the reflected electromagnetic signals indicate that the catheter of the catheter adapter is occluded.

2. The system of claim 1, wherein the housing is integral to the catheter adapter.

3. The system of claim 1, wherein the housing is separate from but connectable to the catheter adapter.

4. The system of claim 1, wherein a distal end of the catheter includes one or more inner facets, outer facets, inner curved portions, or outer curved portions to improve the reflection of the electromagnetic signals.

* * * * *